United States Patent [19]
Baer et al.

[11] Patent Number: 5,728,081
[45] Date of Patent: Mar. 17, 1998

[54] ABSORBENT COMPOSITE ARTICLE HAVING FLUID ACQUISITION SUB-LAYER

[75] Inventors: Samuel C. Baer, Woodbury; Richard S. Yeo, Medford; Ann Marie Noftsier, Vincentown, all of N.J.

[73] Assignee: FiberTech Group, Inc., Landisville, N.J.

[21] Appl. No.: 680,995

[22] Filed: Jul. 16, 1996

[51] Int. Cl.$^6$ .............................. A61F 13/15; A61F 13/20
[52] U.S. Cl. .......................... 604/370; 604/378; 604/367
[58] Field of Search .................... 604/378, 385.1, 604/365, 366, 367, 368, 370, 375, 381, 384

[56] References Cited

U.S. PATENT DOCUMENTS

| | | | |
|---|---|---|---|
| 5,348,547 | 9/1994 | Payne et al. | 604/378 |
| 5,591,149 | 1/1997 | Cree et al. | 604/378 |

*Primary Examiner*—John G. Weiss
*Assistant Examiner*—Ki Yong O.
*Attorney, Agent, or Firm*—Juettner Pyle Lloyd & Piontek

[57] ABSTRACT

An absorbent article has an absorbent core and a liquid permeable top sheet made of polyolefin material. An acquisition layer is provided between the top sheet and the core. The acquisition layer is a nonwoven fabric made from polyolefin fibers bonded by a cured resin. The acquisition layer has a larger pore size than the top sheet and is treated with a surface active agent to render it hydrophilic.

14 Claims, 1 Drawing Sheet

ABSORBENT COMPOSITE ARTICLE HAVING FLUID ACQUISITION SUB-LAYER

BACKGROUND OF THE INVENTION

This invention relates to absorbent composites and more particularly to composites capable of rapidly absorbing liquids, such as disposable diapers or other disposable sanitary products, such as adult incontinence briefs and sanitary pads.

Originally, disposable diapers and related absorbent products were made from a top or cover layer of porous fabric, a central layer of liquid absorbing pulp, and an outer layer of impervious film. More recently, attempts have been made to reduce the bulk of the core, in order to reduce product thickness, for several reasons, such as reduced shipping cost, reduced storage space, and better conformability of the absorbent article or garment to the body of the user.

A reduced thickness of the core has been accomplished primary by increasing the density of the cellulose pulp and by adding up to about 40% of a superabsorbing polymer to the core. These changes, however, inevitably have led to a reduction in the rate of absorption of liquid into the core, resulting in possible runoff and leakage of liquids.

In more recent times, proposals have been made to insert an additional layer of nonwoven fabric between the absorbent core and the porous top sheet, in order to act as a so-called surge or acquisition layer. The purpose of such layer is to allow rapid absorption and distribution of possibly repeated insults of liquid and to allow sufficient time for the core to permanently absorb the liquid.

Commercial products such as diapers have employed various types of fabrics as an acquisition layer. Spunbonded fabrics have been employed, but these typically have a relatively small void volume and cannot accept sufficient quantities of liquid to prevent rewetting of the top sheet or leakage. Bulky acquisition layers are employed, which comprise through-air thermally bonded bicomponent fibers, but such a layer adds undesirable bulk to the final product.

Another fabric used as an acquisition layer is a web made from adhesively bonded polyester staple fibers. Although such webs are employed with success, there still remain disadvantages. For example, the typically top sheet is composed of polypropylene fibers and cannot be thermally or sonically bonded to the polyester acquisition layer, which has a much higher melting point. Rather, the fabrics must be joined with adhesive, which may possibly decrease liquid transfer rate and add to the cost of manufacture. Also, if dissimilar materials are used in the two layers, used products are difficult to recycle.

SUMMARY OF THE INVENTION

In accordance with the present invention, a nonwoven fabric is prepared from polyolefin staple fibers by application of a suitable curable adhesive, preferably in the form of an aqueous suspension of emulsion. The web is then consolidated by heating the fabric to cure the adhesive and cause point bonding between intersecting fibers. If the web is to be employed as an acquisition layer, a surface active agent is either mixed with the adhesive or is subsequently applied to the consolidated fabric in order to render the fabric more hydrophilic.

The present invention also contemplates an absorbent article comprising, in order, a porous top sheet of nonwoven polyolefin material, an acquisition layer made from the above-described web, and an absorbent core. The acquisition layer has a pore size greater than the top sheet. Also, the top sheet and acquisition layer are thermally compatible and can be, or are, thermally bonded together. For example, the top sheet and acquisition layer may be made from the same type of polyolefin fibers such as polypropylene. The polyolefin fibers in the top sheet have an average diameter of from about seven to twelve microns, with the fabric having a basis weight of from about ten to about forty grams per square meter (gsm). The fibers in the acquisition layer have an average diameter of from about ten to about twenty-four microns, and the fabric has a basis weight of from about ten to about one hundred gsm.

DESCRIPTION OF THE PREFERRED EMBODIMENTS

Figure 1:
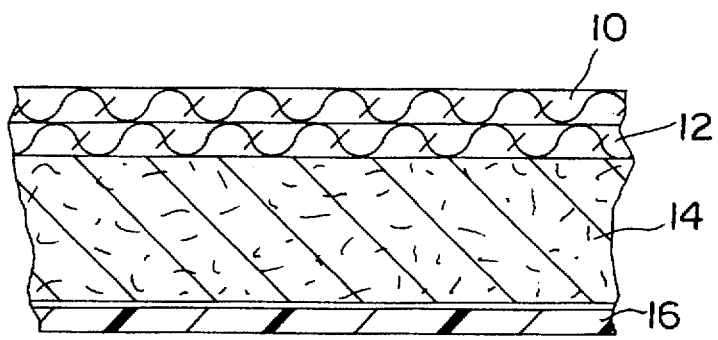
FIG. 1 is a schematic cross sectional view of the liquid absorbing composite of the present invention.

As shown in FIG. 1, the basic components of the present invention comprise a porous top sheet 10 of nonwoven polyolefin fibers, an acquisition layer 12 comprising a web of adhesively bonded polyolefin fibers, and a liquid absorbing core 14. In most cases, the article will include an outer liquid impermeable layer 16 such as a film.

The core 14 may comprise fibers capable of absorbing relatively large quantities of liquid, such as cellulose fibers or wood pulp. The core may also comprise polymers capable of absorption of many times by its weight of liquid. These well known superabsorbent polymers may be employed in powdered or fiber form and are well known in the art of absorbent products.

The top sheet 10 and acquisition layer 12 comprise polyolefin fibers which are thermally compatible and which may be heat or ultrasonically bonded together. Suitable polyolefins include polypropylene, polyethylene, polybutylene, copolymers of such polymers and blends thereof. Polypropylene is preferred. Although less preferred, the fabric layers may comprise bi-component or multi-component fibers having an exposed polyolefin component, such as sheath-core or side-by-side bicomponent fibers. As one example, bicomponent fibers having a polyester core and a polypropylene sheath may be employed.

The top sheet 10 may be made by any suitable conventional method for making nonwoven fabrics. One particularly suitable method starts with the carding of polyolefin fibers into a uniform, random web, and then consolidating the fibers. The preferred method of consolidation is by thermal bonding, such as by passing the web through heated calendar rolls, one of which is engraved, whereby the fibers are thermally point bonded in a repeating pattern. Other suitable methods include entanglement of the fibers such as by hydroentanglement and through air bonding in which heated air is passed through the unconsolidated web.

The diameter of the fibers and the basis weight of the fabric of top sheet 10 relative to the acquisition layer 12 is very important in order to provide an acceptable rate of transfer of liquid towards and into the core 14. The fibers in the top sheet should have an average diameter of from about seven to about twelve microns, with the fabric having a basis weight of from about ten to about forty gsm. The fibers in the acquisition layer 12 should have an average diameter of from about ten to about twenty-four microns, and the fabric should have a basis weight of from about ten to about one hundred gsm.

In addition, the average pore size of the acquisition layer, measured at 0.5 psi is substantially greater than the average pore size of the top sheet 10. For example, the pore size of the top sheet 10 will typically average in the range of about 20 to 50 microns, whereas the pore size of the acquisition layer will be in excess of 50 microns, preferably in the order of about 60 to about 180 microns.

While both the top sheet 10 and acquisition layer 12 may comprise a mixture of fibers including polyolefin fibers, at least a majority of the fibers and preferably in excess of 50 to 65% of the fibers will be thermally compatible, so as to be heat sealable.

The acquisition layer 12 is a web comprising adhesively bonded polyolefin fibers, with the web being treated with a surface active agent to render it more hydrophilic, and typically but not necessarily more hydrophilic than the top sheet 10. The web is formed by carding crimped fibers onto a moving support, treating the fibers with a heat curable adhesive, and then heating the web to cure the adhesive. It is important that the adhesive cure at a temperature below the melting temperature of the fibers.

In the preferred embodiment, the adhesive is applied in the form of an aqueous emulsion. The emulsion may be applied by dipping or by other coating methods, such as spraying, printing or other techniques. The mount of curable resin applied should be in the order of from about ten to about thirty percent by weight solids based on the weight of the fiber.

Depending on the type of adhesive employed, the resin is cured by application of heat to the adhesively treated web. Resins which are curable or cross linked by radiation may also be employed. Either the web may be passed through an oven, or in the case of the polypropylene web, may be passed over steam cans to cure the resin. As the web is dried, the adhesive tends to accumulate at the points of fiber intersection as it is being cured. Suitable resins or adhesives include, for example, styrene-butadiene, ethylene vinyl acetate, ethylene acrylic acid, polyvinyl acetate, styrene acrylic acid, polyurethane, polyvinyl alcohol and chemically modified starch, as well as terpolymers of the polymers or copolymers, such as styrene-butadiene-acrylic terpolymers.

The curing temperature of the adhesive resin is preferably above 105° C. Also, the curing temperature is preferably at least 5° C. below the melting temperature of the fibers in order to prevent any possible thermal deformation of the fibers and fibers sticking to the steam cans. The term "curable or cured" as used herein means that the adhesive is capable of a water resistant bond upon being dried.

The fabric is treated with a surface active agent such as a surfactant to render the web more hydrophilic. The surface agent is applied at a rate of from about 0.1 to about 5 percent by weight of the fibers. Although nonionic surfactants may be employed, anionic surfactants are preferred. The surfactant may be mixed with the aqueous adhesive emulsion prior to application to the web, and in such case, the surfactant must be compatible with the emulsion of latex. Also, at least part of the agent may be applied to the dry web of fibers in the form of an aqueous solution in order to pre-wet the fibers. Another suitable method for application of the surface active agent is application after drying, such as by spraying on an aqueous solution, followed by drying.

In order for the acquisition layer to function properly, the surface tension of the surfactant should be less than 31 dyne/cm at 25° C., and more preferably, less than 28 dyne/cm. The preferred surfactant is a sulfosuccinate and derivatives thereof. Other suitable types include ethoxylated alkylphenols and sorbitan derivatives.

As discussed hereinbefore, the top sheet 10 and the acquisition layer 12 preferably comprise fibers made of the same polymer. For example, if the top sheet 10 is made from a web of thermally bonded polypropylene fibers, the acquisition layer is made from resin bonded polypropylene fibers. This allows the top sheet 10 to be thermally bonded to the acquisition layer by heat or sonic bonding, for example, at spaced locations between the two layers. This feature eliminates the need to apply a separate adhesive between the layers during fabrication of the absorbent article.

The acquisition layer has several advantages over other types which have been proposed or are presently in use. Especially, if polypropylene fibers are used in the fabrics of the top sheet and acquisition layer, the cost of manufacture is kept as low as possible, since polypropylene has a lower density than many other polymers such as polyester. The two layers being of the same polymer, can be more easily recycled. Also, the acquisition layer of the present invention has a low bulk and can be effectively incorporated into present day ultra thin absorbent products.

What is claimed is:

1. An absorbent article comprising a porous top sheet comprising a nonwoven polyolefin fabric, said top sheet having a basis weight of from about 10 to about 40 grams per square meter, an absorbent core, and a porous acquisition layer disposed between said top sheet and said core, said acquisition layer comprising a nonwoven fabric of polyolefin fibers an adhesive bonding said polyolefin fibers together, said acquisition layer having a basis weight of about 10 to about 100 grams per square meter, said acquisition layer having a pore size larger than the pore size of said top sheet and being treated with a surface active agent to render said acquisition layer hydrophilic, said top sheet and said acquisition layer being thermally bonded.

2. The absorbent article of claim 1 wherein the top sheet and the acquisition layer comprise the same polyolefin.

3. The absorbent article of claim 2 wherein said polyolefin is polypropylene.

4. The absorbent article of claim 1 wherein said top sheet is a nonwoven fabric of thermally bonded polyolefin fibers.

5. The absorbent article of claim 1 wherein said top sheet and acquisition layers are thermally bonded in spaced locations.

6. The absorbent article of claim 1 wherein said polyolefin fibers of said acquisition layer comprise bicomponent fibers.

7. The absorbent article of claim 1 wherein said polyolefin fibers of said top sheet comprise bicomponent fibers.

8. The absorbent article of claim 1 wherein said top sheet comprises fibers having a diameter of from about 7 to about 12 microns, and said acquisition layer comprises fibers having a diameter of from about 10 to about 24 microns.

9. The absorbent article of claim 1 wherein said adhesive is present in the mount of from about 10 to about 30% based on the weight of the fibers.

10. The absorbent article of claim 9 wherein said adhesive comprises a styrene butadiene acrylic latex.

11. The absorbent article of claim 9 wherein said adhesive comprises ethylene vinyl acetate.

12. The absorbent article of claim 9 wherein said adhesive comprises ethylene acrylic acid.

13. The absorbent article of claim 1 wherein said surface active agent is a surfactant having a surface tension of less than 31 dyne/cm.

14. The absorbent article of claim 13 wherein said surfactant comprises sulfosuccinates and derivates thereof.

* * * * *